(12) United States Patent
McDerment et al.

(10) Patent No.: US 11,324,900 B2
(45) Date of Patent: May 10, 2022

(54) HINGED CAPSULE INHALER (71) Applicant: HOVIONE TECHNOLOGY LIMITED, Ringaskiddy (IE)

(72) Inventors: Ian McDerment, Royston (GB); Peter Villax, Lisbon (PT); João Ventura, Costa da Caparica (PT); William Richardson, Royston (GB)

(73) Assignee: HOVIONE TECHNOLOGY LTD., Cork (IE)

( * ) Notice: Subject to any disclaimer, the term of this patent is extended or adjusted under 35 U.S.C. 154(b) by 648 days.

(21) Appl. No.: 15/307,309

(22) PCT Filed: Apr. 29, 2015

(86) PCT No.: PCT/GB2015/051246
§ 371 (c)(1),
(2) Date: Oct. 27, 2016

(87) PCT Pub. No.: WO2015/166239
PCT Pub. Date: Nov. 5, 2015

(65) Prior Publication Data
US 2017/0056608 A1 Mar. 2, 2017

(30) Foreign Application Priority Data
Apr. 29, 2014 (PT) .......................................... 107627

(51) Int. Cl.
*A61M 15/00* (2006.01)
*A61M 15/08* (2006.01)

(52) U.S. Cl.
CPC ...... *A61M 15/0026* (2014.02); *A61M 15/004* (2014.02); *A61M 15/0028* (2013.01);
(Continued)

(58) Field of Classification Search
CPC ...... A61M 15/00; A61M 15/0003–001; A61M 15/002; A61M 15/0021; A61M 15/0028;
(Continued)

(56) References Cited

U.S. PATENT DOCUMENTS

| | | | |
|---|---|---|---|
| 4,834,083 A * | 5/1989 | Byram ................ | A61M 15/009 128/200.14 |
| 5,685,294 A | 11/1997 | Gupte et al. | |

(Continued)

FOREIGN PATENT DOCUMENTS

| | | |
|---|---|---|
| PT | 105065 B | 7/2012 |
| WO | WO 2012/047182 A2 | 4/2012 |

(Continued)

*Primary Examiner* — Michael J Tsai
*Assistant Examiner* — Ned T Heffner
(74) *Attorney, Agent, or Firm* — Blank Rome LLP (57) ABSTRACT

A dry powder inhaler (1) for pulmonary or nasal use, employing capsules (6) containing a dose of powder for inhalation, comprising four components: a capsule tray (2), a cover (4) and a mouthpiece (8) and an inhaler body (3). Air is drawn by the patient via the mouthpiece (8) which is in communication with the capsule (6) and travels via air paths through the device (1) and through the capsule (6) thereby dispersing and entraining the dose of powder. The capsule (6) is cut by cutting means (18, 19) located on the body (3). The inhaler body (3), the mouthpiece (8) and the cover (4) are provided with hinge segments (20, 35, 42) which when assembled together and the mouthpiece (8) is locked into the body (3), form a single hinge (5) and which allows the cover (4) to freely pivot around the body (3) and the mouthpiece (8).

6 Claims, 6 Drawing Sheets

(52) U.S. Cl.
CPC .... *A61M 15/0038* (2014.02); *A61M 15/0091* (2013.01); *A61M 15/08* (2013.01); *A61M 2202/064* (2013.01); *A61M 2207/00* (2013.01)

(58) Field of Classification Search
CPC .......... A61M 15/0033; A61M 15/0045; A61M 15/0051; A61M 15/0065; A61M 15/0085; A61M 15/0086–0088; A61M 15/06; A61M 15/08–085; A61M 2202/00; A61M 2202/0007; A61M 2202/06; A61M 2202/064
See application file for complete search history.

(56) References Cited

U.S. PATENT DOCUMENTS

| | | |
|---|---|---|
| 7,878,193 B2 | 2/2011 | Kladders et al. |
| 8,006,695 B2 | 8/2011 | Lulla et al. |
| 8,022,082 B2 | 9/2011 | Zierenberg |
| 8,677,992 B2 | 3/2014 | Villax et al. |
| 2003/0235538 A1* | 12/2003 | Zierenberg ........... A61K 9/0075 424/46 |
| 2004/0118399 A1* | 6/2004 | Young ............... A61M 15/0028 128/203.15 |
| 2007/0283955 A1 | 12/2007 | Tsutsui |
| 2013/0255679 A1* | 10/2013 | Andrade ........... A61M 15/0028 128/203.15 |
| 2013/0269695 A1 | 10/2013 | Brouet et al. |
| 2014/0076315 A1 | 3/2014 | Von Schuckmann |

FOREIGN PATENT DOCUMENTS

| | | |
|---|---|---|
| WO | WO 2012/120419 A2 | 9/2012 |
| WO | WO 2013/095311 A1 | 6/2013 |

* cited by examiner

HINGED CAPSULE INHALER

BACKGROUND OF THE INVENTION

1. Field of the Invention

The present invention describes a re-usable pulmonary or nasal inhaler employing capsules of simple construction and operation and low cost.

Inhalers used for the delivery of pharmaceutical compounds are widely known and they are used for the delivery of several types of medicines treating lung disease and as well as for systemic delivery. Several types of inhalers are known, from those comprising a dosing valve and a pressurized canister, to nebulizers and powder-based inhalers. This latter category includes reservoir-based devices, containing a bulk container of powder from which several doses may be dispensed, or a supply of unit-doses packaged in blisters, or simple capsules which are loaded by the patient, cut by the device and which deliver the dose of medicinal powder under the suction of patient's inspiratory effort. The present device is in this last category.

Capsule-based inhalers, which thus rely on a significant interaction with the patient, present a challenge for the developer. In this type of device, there are several objectives to resolve and they are sometimes contradictory. First of all, in order to make the device easy to use, the number of manual steps required from loading the capsule to inhalation should be desirably few in number, and this is sometimes achieved by increasing the number of inhaler components to produce a device of considerable mechanical sophistication. However, an increased number of components reduces device reliability and results in a significant increase in manufacturing cost and this is relevant because the inhaler is very often the most costly part of a pharmaceutical drug pack. Faced with the requirements of cost-conscious healthcare providers and consumers, whether in established or in emerging markets, the developer is therefore aware that the greatest opportunity in gaining a competitive advantage is closely related to cost reduction in the inhaler.

The developer is thus faced with the dilemma of designing and manufacturing an inhaler which is either too expensive to make (but easy to use), or too difficult to use (but inexpensive to make).

Secondly, an inhaler should be designed not just to have the fewest number of components while retaining ease of use, but it should be designed for easy and economic high speed industrial assembly. This is important as industrial assembly can represent an important proportion of the cost of goods, and the developer should think about device designs which can be easily assembled on an industrial scale.

Thirdly, the reduction in the number of components should not be at the expense of its primary function, which is efficiently converting the patient's inspiratory effort in dispersive and entrainment forces to de-agglomerate and aerosolize the unit dose of pharmaceutical powder, transport it out of the device through the nosepiece or mouthpiece and deposit it in the intended site of action in the nose or in the lungs.

2. Discussion of Prior Art

There is abundant prior art in this field, but solving all of the above requirements has so far eluded the experts in inhalation delivery. The present application is particularly directed at the inventive improvement of the inhaler described in PT105065.

PT105065 describes a capsule based inhaler composed of only two operating components, the body, the tray and an optional cover, where the capsule is loaded from the side into a capsule chamber of the tray. The tray then slides across the body until it stops at the inhalation position. The operation is simple, but in human factors tests, patients suggested that the cover be connected to the device (to simplify handling and avoid losing it) and that the capsule loading action be made easier.

U.S. Pat. No. 5,685,294 discloses a hinged mechanism to attach a movable mouthpiece to the inhaler body but does not provide for a cover intended to prevent dust ingress. The capsule is loaded into a capsule container vertically, when the hinged mouthpiece is lifted to reveal a top-loading capsule compartment. In use, the capsule is pierced by two spring-loaded needles operated by a push-button and the disposition of the air inlets and outlets and the design of the capsule compartment lead the capsule to vibrate and empty under the patient's inspiratory effort. It is a complex construction, comprising at least eight components, which adds to manufacturing cost.

U.S. Pat. No. 7,878,193 discloses an improvement over the previous patent and adds a hinged movable cover. The drawings of this patent show an inhaler device comprising 11 components. U.S. Pat. No. 8,022,082 shows the same inhaler device but with greater detail and the application drawings show 14 separate components. This increased number of components adds to manufacturing and assembly cost.

U.S. Pat. No. 8,006,695 discloses an improvement over the previous patent and adds an internal mechanism whereby the movement of a closure component (in this case, the mouthpiece) leads to a fully extended and then to a fully retracted movement of the piercing needles thereby saving on the number of actuations steps required by the patient when compared to U.S. Pat. No. 7,878,193, as the piercing action is now included in the closing step. This construction however requires several components, precision-built parts and complex assembly for correct and reliable inhaler operation, leading to high manufacturing cost.

PCT application WO 2012120419 discloses an improvement over the previous patents comprising a hinged cover which acts both as a protective element to dust ingress and as a safety element preventing the capsule from being pierced accidentally. This safety element is accomplished by the design of a hinged cover that is pivoted in the button actuating the capsule piercing means and is snap engaged in the inhaler body, thus requiring the cover to be opened in order to unlock the said button. Loading of the capsule is accomplished through a base element that rotates relative to the inhaler body element allowing the user to access to the capsule holder moulded into the inhaler body. However, this construction comprises at least 7 unique components, leading to high manufacturing cost.

WO pat. 2013095311 presents a hinged inhaler construction similar to U.S. Pat. No. 7,878,193 but discloses an improvement based on the inclusion of a safety lock button which allows the release of the cover and mouthpiece elements in a simultaneous manner. This has the advantage of allowing an easier top loading of the capsule into the bottom casing and preventing the accidental release of both elements. The drawings of this patent show a complex construction comprising at least 10 components adding to total manufacturing cost.

US pat. appl. 20130269695 discloses an inhaler comprising a body element, a plate including guide means, a slidable member with a set of teeth and a mouthpiece element, all assembled together by means of a pin element. A distinctive feature is the use of a tinted transparent material that is adapted to filter UV rays and makes it possible to see the inside of the inhaler body while masking residues of powder that may be left after inhalation. During operation, opening the mouthpiece element allows the top loading of the capsule into the body and the closing operation causes the slidable member to break the capsule in two portions, which allows subsequent inhalation of its contents. Drawings show a construction comprising at least 8 components including precision built elements and a complex assembly sequence, leading also to high manufacturing cost.

US pat. appl. 2014076315 presents a hinged inhaler construction which further discloses an improvement relative to previous patents consisting in placing the air inlet to the mouthpiece adjacent to and under the hinged cover. This lateral offset has the advantage of avoiding accidental air blockage during inhalation and facilitating cleaning. The drawings disclose a snap type of hinge connecting the inhaler cover element to the mouthpiece element that enables the pivot position of the cover to be locked in the open position. However, the construction disclosed comprises at least 7 unique components which also add to high cost.

There is therefore a need for a capsule-based powder inhaler which achieves the functionality of the hinged inhalers described in the above patents, comprising at least a mouthpiece, a capsule holder, a piercing mechanism and a cover designed, manufactured and assembled to achieve the lowest possible cost in a device where operation is easy and readily apparent to the patient. The expert in the art will recognise that this goal can be achieved not just by improving the existing devices, but by radically re-inventing the components in a way which results in a novel way to assemble and operate them.

SUMMARY OF THE INVENTION

We have now invented a hinged inhaler comprising only four plastic moulded parts where three of them are designed for assembly around a single pivot point and when assembled constitute an inhaler having only three movable parts and where only two of those movable parts are actually needed for inhalation. To have this number of components constitutes a clear economic advantage and an inhaler that is reliable and easy to use.

The present invention comprises four plastic-injected moulded components: a cover, a mouthpiece, a body and a tray. The cover, the mouthpiece and the body comprise moulded features which, when joined together, form a hinge, without the need or addition of any other mechanical components, and this is new.

In the assembly process, the tray is inserted into the body, where it is able to freely slide across the guiding slides in the body. The assembly then includes joining the cover to the body and then to the mouthpiece and locking them into place so that the mouthpiece and body constitute a single, locked, integral component and the cover is able to move and pivot relatively to said mouthpiece and body. In use, the tray is able to slide inside the body but the travel of the movement is limited by mechanical features in the body. As the body and mouthpiece are locked together, the travel of the tray is constrained and it can no longer slide completely out of the body.

The action of joining together the body containing the tray to the cover and then to mouthpiece, around a single pivot point, where the pivot point is formed of hinge elements which are integrally moulded as part of each of the body, the cover and the mouthpiece, provides for a functional inhaler and this is new.

The inhaler of the present application includes features found in the inhaler described in PT 105065 and the common features are now detailed.

As in PT105065, the inhaler tray is provided with a capsule chamber of a dimension suitable to freely receive a capsule. Preferably it is made of transparent plastic so that the patient can verify that it has been suitably inserted. The tray is sized so that it can fit inside an opening in the body. The tray is provided with guides which will adjoin the body, so that the tray can freely slide inside the body. The tray is provided with an air inlet at the bottom of the capsule chamber so that air may be admitted to the capsule.

The inhaler body is also provided with an opening comprising four walls which will contain the tray and allow it to slide within in a controlled movement. It is further provided with mechanical features which provide stops to the sliding motion of the tray to keep this motion within a suitable operating range and prevent the tray from fully exiting the body opening, so that the tray is always contained inside the body opening. The four walls are a top wall, a bottom wall, a front wall and a back wall. The body comprises two plastic blades which are moulded in the same manufacturing step as the body and preferably of the same material, one or more air inlets which allow the passage of air into a mouthpiece channel and an opening in the top wall which can receive an inhalation channel. In both inhalers, the blades are double-sided, meaning that they have a leading edge and a trailing edge, able to cut the capsule on the way in, for inhalation, and on the way out, for ejection.

As in PT105065, the inhaler mouthpiece or nosepiece is shaped and deprived of any sharp features to provide a comfortable and safe means for the user to place its mouth or nose before inhalation. An inner inhalation channel with a designed aerodynamic shape is provided across the mouthpiece longitudinal axis that allows the admission of air through one or more air inlets provided in the mouthpiece which allows the transportation and dispersion of the powder from the capsule to the patient's respiratory tract during inhalation.

As found in PT105065, the inhaler cover is shaped to provide a means of protecting the mouthpiece element of the ingress of foreign particles during storage and it is provided with a surface area where user instructions can be painted, printed, etched or engraved.

The inhaler of the present application includes new features not found in the inhaler described in PT 105065 or in the prior art and they are now detailed.

In this new inhaler, the cover, mouthpiece and body all comprise integrally moulded hinge segments which include one or more bearing surfaces, which when assembled together result in a complete hinge which mechanically joins all of the inhaler components together and create a functional inhaler. The hinge element on the cover is an axle, which when assembled with the mouthpiece hinge segment and the body hinge segment results in a complete hinge that allows the cover to freely pivot around the body and the mouthpiece. In other constructions the axle could be on the body or on the mouthpiece, but the preferred embodiment places it on the cover.

Furthermore, the body and the mouthpiece comprise one or more moulded recesses and one or more moulded pins which, which are pressed to mechanically lock the mouthpiece component and the body component together. Such pins and recesses are placed in the body and mouthpiece so that they are properly aligned to engage and lock into place either by friction or snap-fit, but snap-fit is preferred. A snap-fit means that the assembly can lock, but not unlock without tools.

The cover and the mouthpiece also include similar recesses and pins, so that the cover may lock in the shut position when not in use and this is provided by a friction fit or an interference fit between cover and mouthpiece, which is designed and manufactured so that the cover remains shut during transport, but may be easily opened by the patient prior to use. A friction or interference fit means that the assembly can lock and unlock using normal patient force. Since the closing and opening point of contact of the cover and mouthpiece is close to the body as well, this point of contact could be placed in the body in other embodiments.

Two features are found in the inhaler of the present invention which are not present in the inhaler of PT015065. One is that the tray comprises a chamber for loading a capsule from the top (in the inhaler of the prior art the tray was side-loading) and the other is that the inhaler includes a mesh or grid to prevent capsule debris from flying into the mouthpiece channel and to support powder deagglomeration and dispersion (the inhaler for the prior art did not have this mesh). However both features are known in the prior art.

During assembly, the tray is inserted into the opening of the body. Then the cover is assembled by placing its hinge segment on the hinge segment of the body. Then the mouthpiece hinge segment is placed on the two other hinge segments so as to form a complete hinge. When the mouthpiece is lowered and locked into position into the body through the engagement of the pins and recesses, the hinge is made permanent and mechanically effective. The hinge pivots around the axle comprised in the cover's hinge segment and the mouthpiece acts as the locking mechanism for the entire assembly. There is thus no need for an additional pin or other separate mechanical element to lock the hinge, as each of the three hinge segments in the body, mouthpiece and cover provide notionally one third of the full hinge. Such novel construction allows the reduction of part count to four unique components and a reduction in the number of steps required to assemble the inhaler to three, both contributing to lower total manufacturing cost and consequent economic advantage.

Generally, the hinge needs to be sized to allow the cover axle to pivot with mechanical clearance inside a circle formed by two complementary, semi-circular load bearing surfaces provided in the body and mouthpiece hinge segments to support the axle and allow the intended pivoting movement of the cover. In a preferred embodiment, we prefer to dimension the diameter of the cover axle between 4.95 and 5.05 mm and the diameter of the semi-circular bearing surfaces of the body and mouthpiece hinge segments between 5.12 and 5.22 mm and the clearance profile allows for a comfortable pivoting of the hinged cover. Generally, the length of the cover axle support in the bearing surfaces provided in the body and mouthpiece hinge segments needs to be sized to provide a mechanically stable and comfortable pivoting movement. In a preferred embodiment, we prefer to dimension the length of the cover axle and the body and mouthpiece hinge segments between 10.4 and 10.5 mm and this allows for a stable and comfortable pivoting of the hinged cover.

Based on these advantages, it is thus an inventive step of the present application that the inhaler has a single hinge, composed of three distinct hinge segments, constructed into the body, mouthpiece and cover components.

It is also an inventive step of the present application that each of the three hinge segments of the body, mouthpiece and cover form a single, permanent and mechanically effective hinge when assembled together and when the mouthpiece component is pressed and locked into the body, through an integral locking mechanism.

It is also an inventive step of the present application that each of the body and mouthpiece hinge segments comprises one or more bearing surfaces and the cover hinge segment comprises an axle, which when joined form a permanent and effective hinge, without the need or addition of any other separate pin or mechanical component.

It is also an inventive step of the present application that the inhaler is constructed from four parts only where the mouthpiece acts as a locking mechanism for the hinge.

It is also an inventive step of the present application that the tray is able to slide across its operating range and is unable to slide beyond this range by the fact that the body, cover and mouthpiece are assembled together at a hinge and the mouthpiece is locked in place into the body.

It is also an inventive step of the present application that the tray is movable inside the body and can be moved outside the body for capsule loading, while the cover is closed. Should the mouthpiece become detached from the body, either through accident or misuse, then the inhaler ceases to be operational and ceases to be an inhaler—only a collection of plastic components.

It is also an inventive step of the present application that the inhaler is composed of four components (the mouthpiece, the body, the tray and the cover) where two of them (the body and the mouthpiece) are locked together so that the inhaler is composed of only three integral components, which are the cover, the mouthpiece locked into the body and the tray. An integral component is one which after assembly operates as a single mechanical element.

The inhaler components described in the present invention can be made by injection-moulding and use any grade of pharmaceutically suitable grade such as polycarbonate (PC), polypropylene oxide (PPO), polybutylene terephthalate (PBT) polyethylene terephthalate (PET), liquid crystal polymer (LCP), polyethyleneimine (PEI), polyphenylenesulphide (PPS) polyethylene (PE) polypropylene (PP), polysulfone (PSU), acrylonitrile butadiene styrene (ABS), polymethylmetacrilate (PMMA), Fortron. The polymer can be natural or glass filled. However, when the blades are injected-moulded together with the inhaler body, they will be made of the same material and a hard plastic material is preferred. Grades such as PC, PPO, PBT, PET glass filled, PPS, PSU, ABS are indicated.

Useful capsules for the inhaler of the present invention include conventional pharmaceutical grade capsules, made of gelatine, polyethylene or cellulose/HPMC, of any size, such as size number 3, or any other size. They can also include custom-designed capsules, made of any other suitable material, including plastic.

In use, the patient requires four inhaler movements to prepare for inhalation. The patient initially pushes the tray sideways into the open position, until the capsule chamber is visible for loading (first movement). The capsule containing a unit dose medicinal powder is then loaded into the capsule chamber by the patient (second). Then the patient pushes the tray in the opposite direction into the body and this cuts the capsule ends as the capsule is pushed past the two blades moulded into the body (third). When it is fully closed, the tray stops in the inhalation position to bring the capsule into alignment with the mouthpiece channel and the capsule remains visible through two windows provided in the body. The patient then opens the cover (fourth) and inhales by placing the mouthpiece into the mouth or nosepiece into the nose.

Under the patient's inspiratory effort, air lifts the capsule towards the mouthpiece channel, and the capsule dome fits exactly the mouthpiece channel opening, so that suction through the mouthpiece and admitted through the mouthpiece and air inlets, forces air to be drawn through the capsule, leading to aerosolization of the powder contained therein and to its entrainment into the mouthpiece, and then into the mouth (or nose) and finally into the intended site of treatment such as the nasal cavity or the lung.

Once inhalation has taken place, the patient closes the cover, pushes the tray out of the body, until the capsule chamber is visible, turns the inhaler upside down, and the spent capsule falls out under gravity.

BRIEF DESCRIPTION OF THE DRAWINGS

So that the invention and its advantages may be more readily understood, there will now be described a preferred embodiment thereof, given by way of example, reference being made to the accompanying drawings, in which.

DETAILED DESCRIPTION OF THE INVENTION

The preferred embodiment herein described comprises the inventive features detailed in the present application and the person skilled in the art will be able to apply the same teachings to other inhalers so these descriptions in no way limit the invention to the embodiment described.

Figure 1:
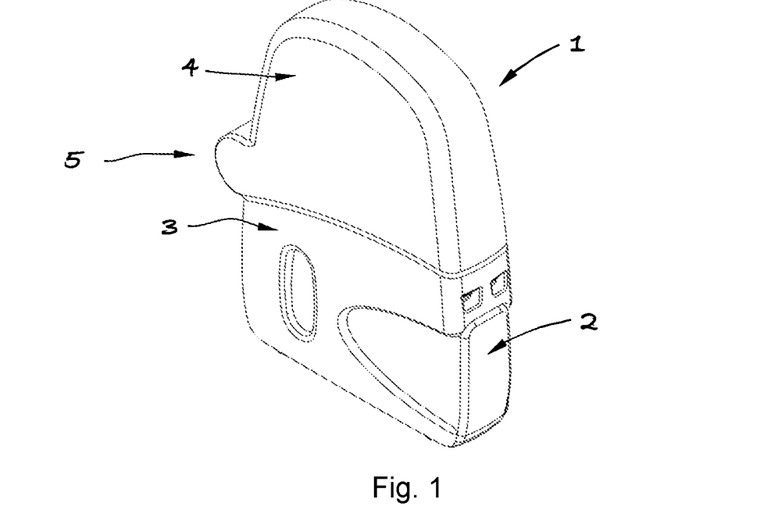
FIG. 1 shows a perspective view of an inhaler according to the invention in the storage position, with the cover closing the device.

Referring to the drawings in FIG. 1 component 1 designates an inhaler of the invention which comprises an inhaler tray 2, an inhaler body 3 and an inhaler cover 4. Numeral 5 indicates the hinge and hinge area.

Figure 2:
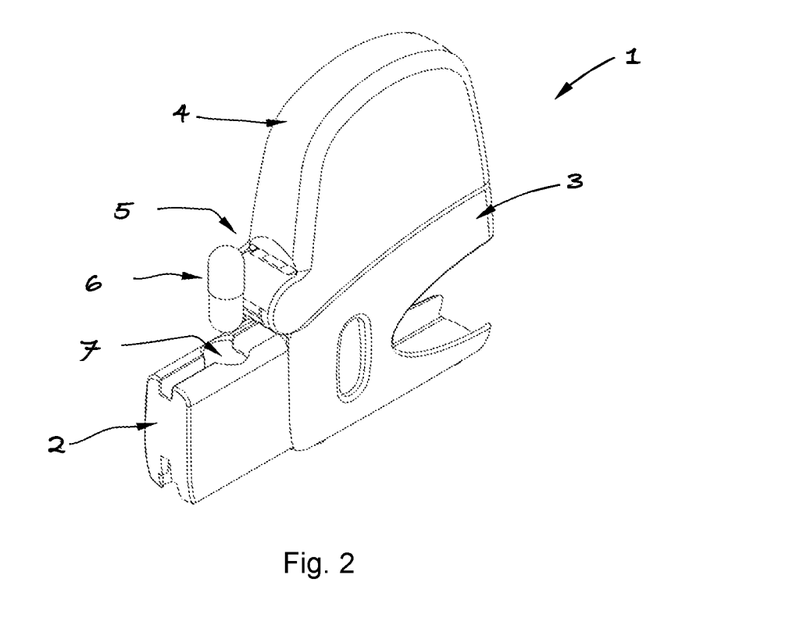
FIG. 2 shows a perspective view of the inhaler of FIG. 1 with the inhaler tray in an open position making the device available for receiving a capsule.

FIG. 2 illustrates the inhaler with the tray 2 pushed into the open position, revealing a capsule 6 ready for loading into capsule chamber 7. The chamber 7 is shaped to receive a capsule 6. Other components are as identified in FIG. 1.

Figure 3:
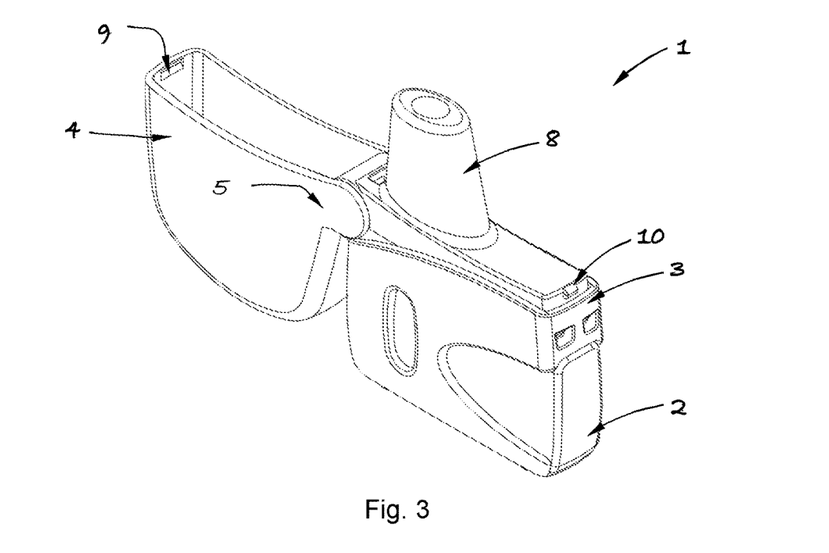
FIG. 3 shows a perspective view of the an inhaler according to FIG. 1 with the inhaler tray loaded and closed, the cover opened and in a position ready for inhalation.

FIG. 3 illustrates the inhaler with the tray 2 in the closed position and the cover 4 in the open position revealing the mouthpiece 8. There is also shown recess 9 in the cover and pin 10 in the mouthpiece 8, which engage when the cover is closed. Other components are as identified in the previous figures.

Figure 4A:
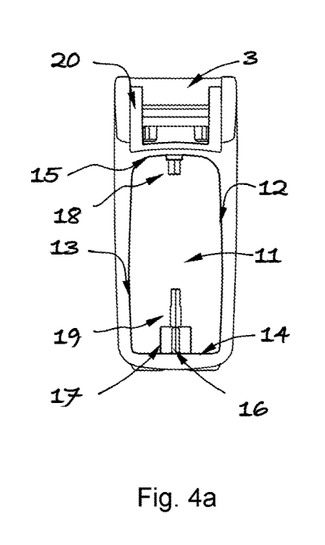
FIGS. 4a to 4b show respectively a side and longitudinal sectional views of the inhaler body component of FIG. 1.

FIG. 4a illustrates a transversal section view of the body 3 having an opening 11, the opening being formed by side 12 and 13 walls and opposing lower 14 and upper 15 walls. The body further includes rail guide 16, sliding detent 17, top cutting blade 18 and lower cutting blade 19. The opening 11 is shaped to receive the tray and rail guide 16 and walls 12, 13, 14 and 15 are constructed to guide the tray movement.

Figure 4B:
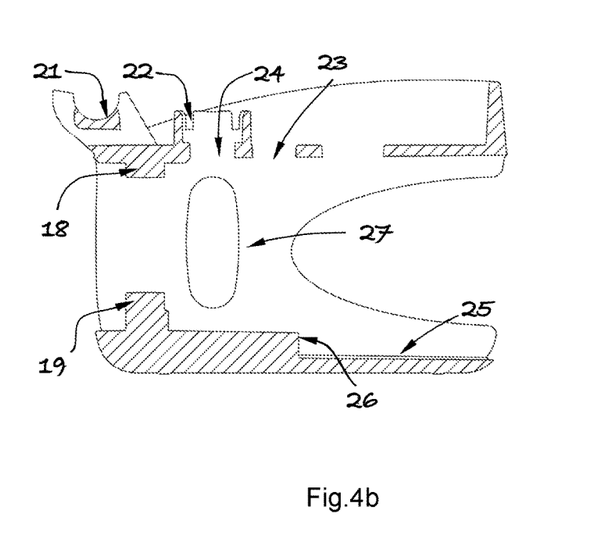

FIG. 4b illustrates a longitudinal section of the body 3 comprising a load bearing surface 21 of the body hinge element 20, air passages 22, an opening 23, an inhalation passage 24, top blade 18 and lower blade 19. There is further a bottom rail 25, a bottom sliding detent 26 and a window 27.

Figure 5:
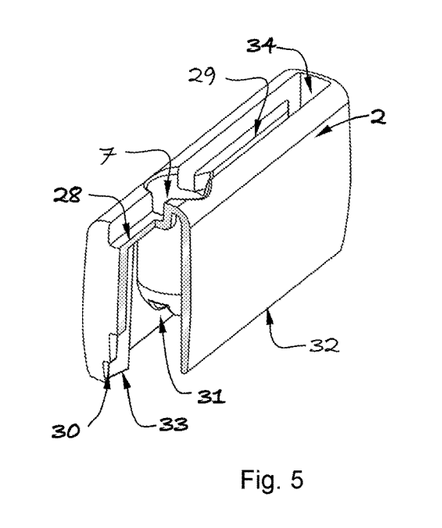
FIG. 5 shows a perspective view but partially cut away of the inhaler tray component of FIG. 1.

FIG. 5 is a perspective, partially sectioned view of the tray, showing tray 2, a capsule chamber 7, top tray openings 28, 29 and a bottom tray opening 30, as well as an air inlet 31 designed to admit air to the bottom hole in the capsule 6, after it has been cut so that inhalation air may be drawn through the capsule. There are also tray bottom walls 32 and internal walls 33, 34.

Figure 6:
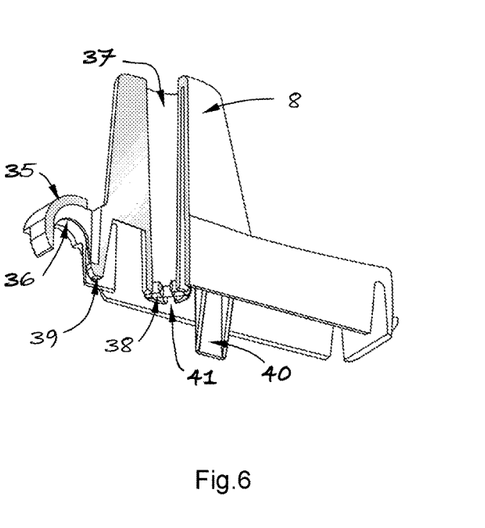
FIG. 6 shows a perspective view but partially cut away of the inhaler mouthpiece component of FIG. 1.

FIG. 6 is a perspective, partially sectioned view of the mouthpiece 8, showing bearing surface 36 of mouthpiece hinge element 35, inhalation channel 37, mesh 38 and pins 39. There is also shown mouthpiece detent 40 and air passages 41.

Figure 7:
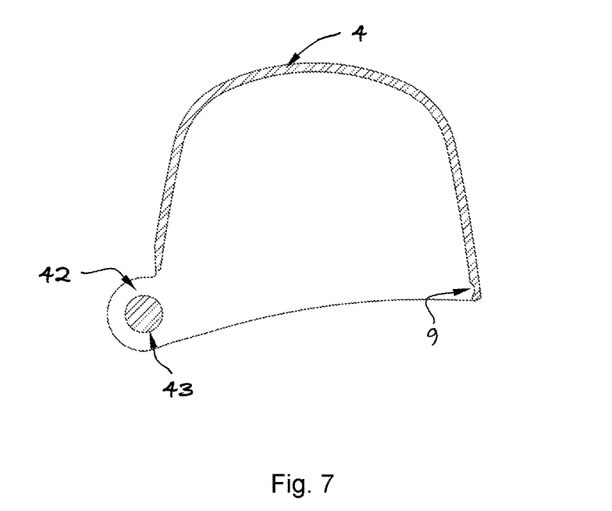
FIG. 7 shows a longitudinal sectional view of the inhaler cover component of FIG. 1.

FIG. 7 is a longitudinal section view of cover 4, comprising an axle 43 of cover hinge element 42. There is also shown the recess 9.

Figure 8:
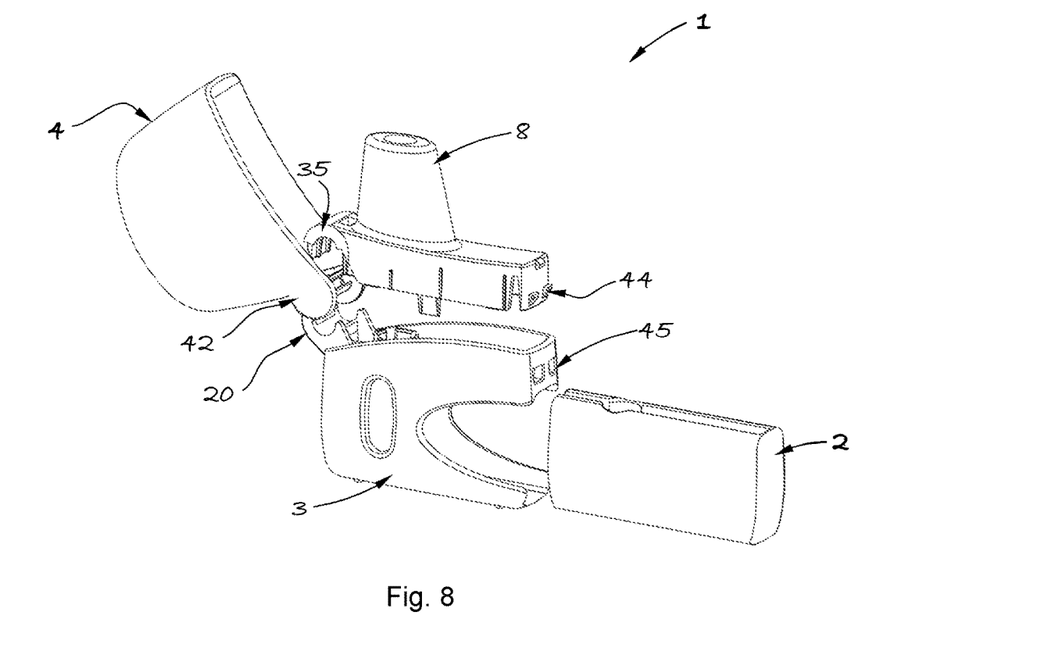
FIG. 8 shows an exploded perspective view of an inhaler according to FIG. 1.

FIG. 8 is a perspective view of the unassembled components of inhaler 1, illustrating mouthpiece pins 44 and body recesses 45, as well as body hinge element 20, mouthpiece hinge element 35 and cover hinge element 42.

Figure 9:
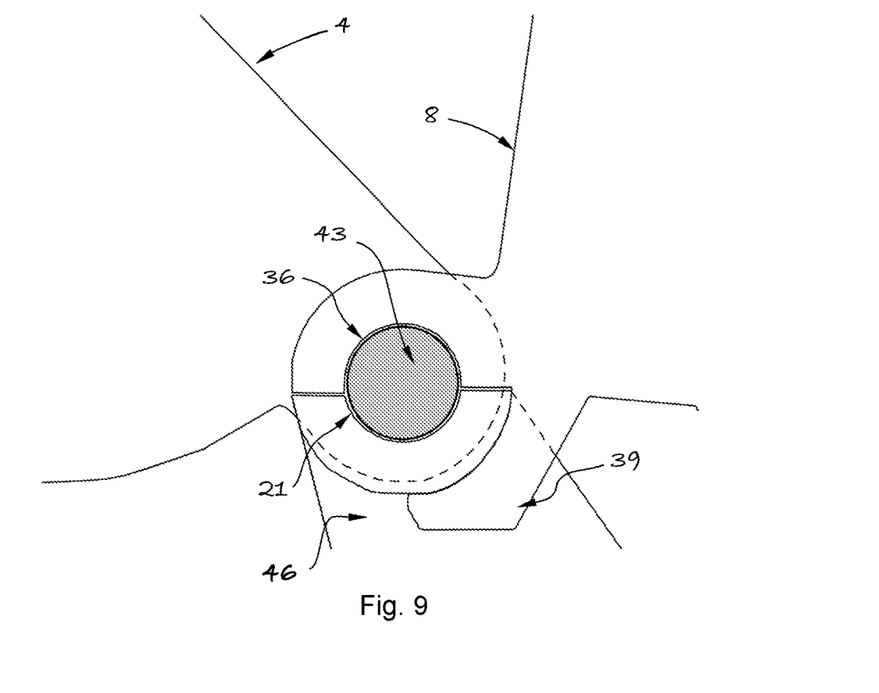
FIG. 9 shows a detailed sectional view of the hinge area of an inhaler according to FIG. 1.

FIG. 9 is a detailed section view of the assembled hinge 5 of inhaler 1, showing load bearing surface 21 of the body hinge element 20, load bearing surface 36 of the mouthpiece hinge element 35, and axle 43 of cover hinge element 42, in the final assembled position, made permanent by the locking of mouthpiece pins 44 and body recesses 45 and by the locking of mouthpiece pins 39 and body recesses 46.

Figure 10:
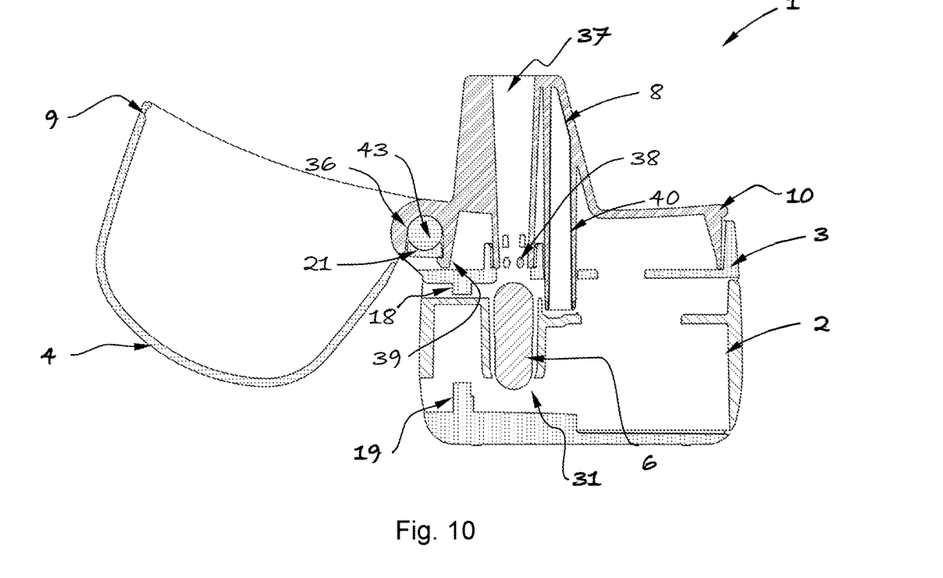
FIG. 10 shows a longitudinal sectional view of an inhaler according to FIG. 1 with the inhaler tray loaded and closed, the cover opened and in a position ready for inhalation.

FIG. 10 is a longitudinal section view of the assembled inhaler 1, illustrating the assembled hinge 5 in the final assembled position with the tray 2 loaded with a capsule 6 and closed into the body 3, the cover 4 opened and in a position ready for inhalation through mouthpiece 8. Other components are as identified in the previous figures.

Figure 11:
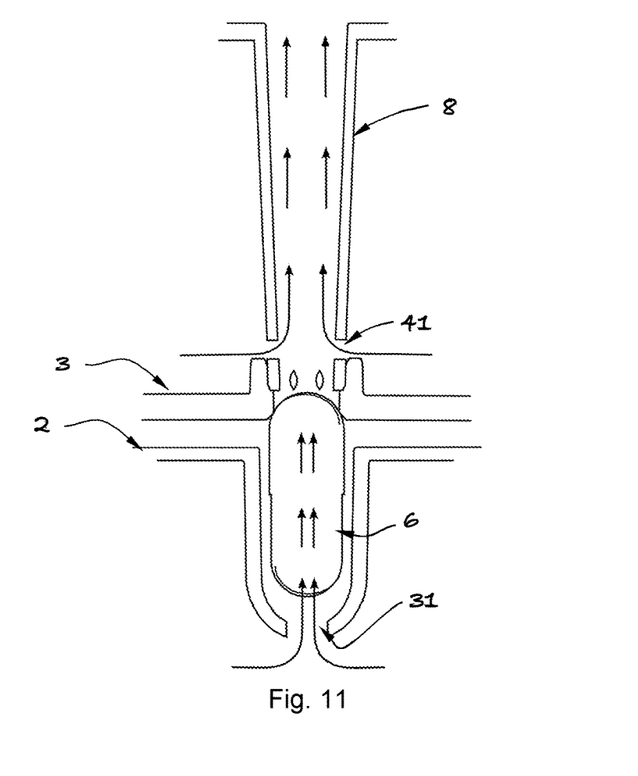
FIG. 11 shows a detailed perspective sectional view of the mouthpiece air inlets area of an inhaler according to FIG. 1.

FIG. 11 is a detailed perspective section view of the assembled mouthpiece 8 of inhaler 1, showing passages 41 there included which become aligned in the final assembled position with the passages 22 comprised in the body 3 to allow the admission of air into the mouthpiece inhalation channel 37.

Figure 12A:
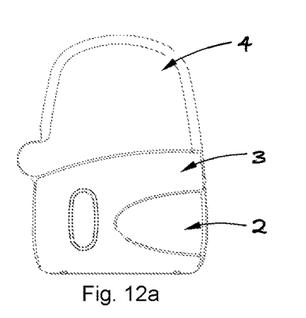
FIGS. 12a to 12f show the sequence of operational steps to load, open, inhale and unload the inhaler of FIG. 1.
Figure 12B:
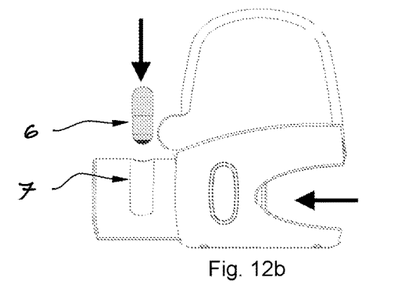
Figure 12C:
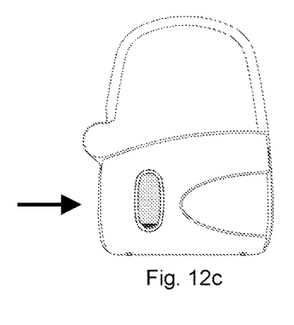

FIGS. 12a to 12f show the inhaler in operation. FIG. 12a shows the inhaler in the storage position. FIG. 12b shows the tray 2 being pushed open and a capsule 6 being inserted into capsule chamber 7. FIG. 12c shows the tray being closed, which cuts the capsules top and bottom and aligns the capsule with the mouthpiece 8.

Figure 12D:
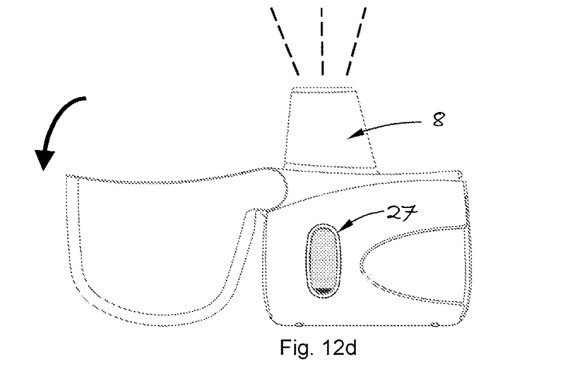
Figure 12E:
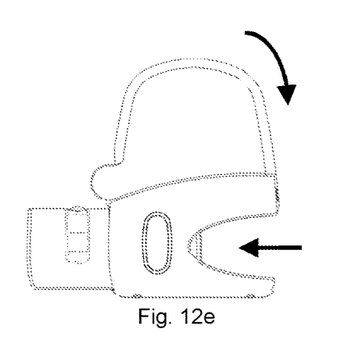
Figure 12F:
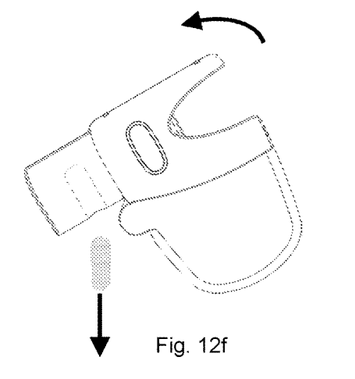

FIG. 12d shows the cover 4 being opened and the inhaler being ready for inhalation. FIG. 12e shows the cover 4 being closed and the tray 2 being pushed open. FIG. 12f shows the inhaler being turned upside down and the capsule 6 falling as a result of gravity.

In assembly, tray 2 is inserted into body 3 and rail 16, bottom rail 25, side walls 12 and 13, bottom wall 14 and top wall 15 guide the tray through engagement with tray walls 32 and opening 30. Then the cover 4 is lowered into place, in the open position, with its axle 43 engaging into the load bearing surface 21 of the body hinge element 20. Finally the mouthpiece is dropped into place, with the load bearing surface 36 of the mouthpiece hinge element 35 contacting first the axle 43 of cover hinge element 42. The assembly is locked into place by pivoting and lowering the mouthpiece 8 around the load bearing and axle surfaces of the hinge formed by the body 3, mouthpiece 8 and cover 4, until the pins 39 of the mouthpiece engage and snap into recess 46 of the body and, on the other side, towards the hinge side, the pins 44 of the mouthpiece engage and snap recess 45 of the cover. The inhaler is now assembled, the cover can be closed shut through the engagement of cover recess 9 and mouthpiece pin 10 and the inhaler is ready for use.

A complete, permanent and mechanically effective hinge 5 is formed, since the axle 43 is allowed to pivot inside a circle formed by two complementary, semi-circular load bearing surfaces 21, 36 which provide load support while allowing the intended pivoting movement of the cover 4. The hinge 5 is made permanent by the mouthpiece pins 39, 44 engaging into the body recesses 45, 46. The hinge assembly turns the various components into a functional inhaler.

When the mouthpiece 8 and the body 3 are assembled, the inhalation channel 37 and the inhalation passage 24 are aligned and define a straight air path. Furthermore, the air passage 22 on the body 3 and the air passage 41 on the mouthpiece 8 fit together to form precise air inlets which channel additional air into the mouthpiece channel 37 and provide for a comfortable inhalation.

Thus the changes suggested by the human factors study conducted on the inhaler of PT105065—an integral cover and a top-loading capsule chamber—were achieved by increasing the part count by just one in the inhaler of the present application when compared with the inhaler of PT105065 and this was made possible by inventing a hinge assembly which makes use of the available parts, without the need or addition of any other component and this is an important economic benefit and a reliability advantage.

In mechanical use, when pushing the tray 2 into the open position of FIG. 2, the movement and travel distance of the tray 2 inside the body 3 is allowed by openings 28, 30 and limited by the contact of tray inner walls 34 with a top sliding detent 40 provided in the inhaler mouthpiece 8 and a bottom sliding detent 26 provided in the body 3. This allows a controlled sliding movement with low frictional resistance of the tray 2 within the body opening 11.

When pushing the tray 2 back into the closed position of FIG. 1, the movement and distance of travel of the tray 2 is controlled by the contact of inner walls 33 provided in the tray 2 with bottom sliding detents 17 provided in the body 3, as shown in FIGS. 4 and 5. The engagement between the tray walls 33 and the body detents 17 provides the mechanism for correct alignment of the capsule chamber 7 in the tray 2 with the inhalation passage 24 provided in the body 3 shown in FIG. 4.

Mechanical interference of the bottom blade 19 to allow its leading edge to come into contact with the capsule 6 is provided by the capsule chamber opening 31 and access is allowed by the tray opening 30. Access of the top blade 18 to allow its leading edge to come into interference with the capsule 6 is provided by the top opening 28 shaped in the tray 2 as shown in detail in FIG. 5.

Capsule cuts are made thin through blade design to prevent accidental powder spilling before the powder contents of capsule 6 are inhaled. Cutting accuracy and reproducibility is ensured through the correct choice of material for the body component 3, as the blades 18, 19 are moulded in the same step as the body and are made of the same material. Proper cutting is ensured through vertical and lateral mechanical constraint of the capsule 6 provided by geometric sizing of the diameter and height of the capsule chamber 7 and also of the height of the blades 18, 19.

Top and bottom openings 29, 30 shown in FIG. 5 are provided in the inhaler tray 2 to allow the flow of air from stagnation conditions through the capsule chamber opening 31 into the capsule 6 after it has been opened by the body cutting blades 18, 19. The air flow passing through the opened capsule provides the means for the powder therein contained to become dispersed and travel out of the capsule 6 into the inhalation channel 37 incorporated in the mouthpiece 8 and detailed in FIG. 6, passing through the inhalation passage 24 provided in the body 3.

Referring to FIG. 6, one or more additional passages 41 are provided in the mouthpiece 8 for the tangential admission of air into the inhalation channel 37 at a location downstream of the inhalation passage 24 included in the body component 3. The additional air flow allowed through the air inlets 41 detailed in FIG. 6 provides the means to reduce the patient's inspiratory effort and to increase the turbulence energy across the mouthpiece channel 37, thus contributing to an effective powder deagglomeration and dispersion. To allow the additional admission of air into the mouthpiece inhalation channel 37, passages 22 detailed in FIG. 4 are provided in the body 3 which become aligned with the air inlets 41 incorporated in the mouthpiece 8 after assembly.

In use by the patient, the inhaler tray 2 is first pushed open as shown in FIG. 12b. Then the capsule 6 is loaded into the capsule chamber 7 and the patient pushes the tray 2 back in the opposite direction, as shown in FIG. 12c. This movement causes the capsule 6 to pass through the leading edge of the cutting blades 18 and 19 detailed in FIGS. 4a and 4b, which cut the top and bottom extremities of the capsule 6. This produces thin top and bottom cuts in the capsule 6 and these cuts are aligned longitudinally with the axis of the capsule. Such thin cuts prevent the powder from spilling out of the capsule prior to inhalation.

The patient then opens the cover 4 (FIG. 12d), empties his or her lungs by blowing away from the inhaler, places the mouthpiece 8 in the mouth or nose and inhales. The resulting suction applied to the straight air path formed by the inhalation channel 37 and by the inhalation passage 24 causes the capsule, which is in alignment with said straight air path, to surge up and block the inhalation passage 24, forcing air to travel through the capsule chamber inlet 31 and into the capsule 6 via the bottom cut in said capsule caused by blade 19. The air aerosolizes the medicinal powder dose and entrains it via the top cut in said capsule caused by blade 18, into the inhalation passage 24, past the mesh 38, into the inhalation channel 37 and finally into the patient's airways. At the end of the inhalation the patient can see through window 27 whether the capsule (made preferable of transparent material) is empty. If it is not, the patient can repeat the inhalation.

The patient then closes the cover 4 and pushes the tray 2 into the open position, as shown in FIG. 12e. As the capsule 6 is driven again past blades 18 and 19, it comes into contact with the blade trailing edges. These trailing edges will again cut the capsule as the tray 2 is opened. In some cases, as the capsule may have been weakened by the first cutting action when the tray 2 was closed after initial loading, now as the capsule 6 exits the trailing edges of the blades 18 and 19 may deform the capsule extremities of the capsule 6, instead of cutting them a second time. However, this does not affect the successful ejection of the used capsule 6 or the operation of the inhaler.

To eject the used capsule 6, the patient turns the inhaler upside down for the capsule to drop out of the capsule chamber 7 through gravity as shown in FIG. 12f. The tray can then be brought to its closed position, ready for the next use.

Example

An inhaler embodiment of the present invention has been tested in vitro to determine its aerodynamic profile as well as its powder dose delivery. An experimental lactose based blend comprising tiotropium at a dose of 18 micrograms per capsule was formulated with lactose (total capsule fill weight 5.5 mg) to determine the dispersion and pharmaceutical efficacy of the inhaler.

After blending of the formulation components to produce an ordered mix and determining the batch homogeneity, the formulated powder was filled using a Flexalab capsule filling machine (MG2, Italy) into cellulose HPMC capsules, size 3 (Capsugel, USA) to be used in the device. The inhaler was then tested at a flow rate of 39 litres per minute and a pressure drop of 4 kPa on a Next Generation Impactor (Copley Scientific, UK), actuated twice to allow a volume of 2×2 litres of air to pass through the device and the mass of active drug deposited at each stage of the cascade impactor was quantified using high pressure liquid chromatography. From these data, the emitted dose and the fine particle dose were calculated, where the emitted dose was the sum of all drug masses collected from each of the impactor stages, including the inductor throat, and the fine particle dose was the mass of drug collected below the 5 micron cut-off point. The ratio of the fine particle dose to the emitted dose is the fine particle fraction and is a measure of inhaler efficiency. The higher the fine particle dose, the higher the lung dose is expected to be. The results are summarized in the following table:

|  | Delivery performance |
|---|---|
| Emitted dose ED | 9.3 mcg |
| Fine particle dose FPD | 3.1 mcg |
| Fine particle fraction (ED/FPD) | 33.3% |

This data indicates that the inhaler embodiment of the present invention is capable of effectively delivering a dose of an inhalation drug, under inspiratory effort conditions which are compatible with the ability of patients.

The invention claimed is:

1. A dry powder inhaler suitable for pulmonary or nasal delivery, the inhaler comprises a cover, an inhaler body, a mouthpiece and a capsule tray,
wherein the inhaler body has
opposing upper and lower walls spaced apart to form a chamber within the inhaler body which constitutes an inhaler body opening, one end of the inhaler body being open by means of which the capsule tray is engageable into the inhaler body opening,
cutting means provided on the upper and lower walls, which cutting means extend into the inhaler body opening,
an inhalation passage formed in the upper wall of the inhaler body, and
a first hinge segment, wherein the first hinge segment includes at least one bearing surface and a body recess;
wherein the mouthpiece includes an inhalation passage, a mouthpiece top sliding detent, and a second hinge segment, the second hinge segment being complementary to the first hinge segment and which includes at least one bearing surface and a mouthpiece pin, the mouthpiece being engageable with the inhaler body such that the first and second hinge segments engage with each other such that the mouthpiece pin engages with the body recess to form a hinge passage between the first and second hinge segments; and
wherein the cover include s a third hinge segment comprising an axle, the axle being integrally molded with the cover and the axle being sized to be engageable in the passage formed between the first and second hinge segments so as to be rotatable within said passage and thereby enable pivoting movement of the cover relative to the inhaler body and the mouthpiece, wherein the first and second hinge segments, respectively, include complementary locking means operable to secure the first and second hinge segment together around the axle;
the capsule tray is moveable in the opening through said open end between a first position in which the capsule tray is withdrawn from the opening so as to allow access to a capsule chamber formed therein for loading and unloading a capsule from the capsule chamber, and a second position in which the capsule chamber is aligned with the inhalation passage of the inhaler body to enable inhalation of the medicament contained in the capsule through the inhalation passage, the cutting means being positioned to engage the top and bottom of the capsule as the capsule tray is moved from its first position to its second position in order to cut openings in the top and bottom of the capsule, at least one of the inhaler body and the mouthpiece including stop means located within the opening which are engaged by the capsule tray as it is engaged into the opening to limit the travel of the tray inside inhaler body opening;
wherein the first hinge segment is semi-circular, partially surrounds the axle, and is sized to support the axle, the second hinge segment is semi-circular and partially surrounds the axle, and the first hinge segment and second hinge segment, together, fully form a circle surrounding the axle when the first and second hinge segments are secured around the axle;
wherein the first hinge segment, second hinge segment and the third hinge segment, when assembled, align the mouthpiece top sliding detent to pass through a body opening such that when said mouthpiece is engaged in the inhaler body, the mouthpiece top sliding detent comes into mechanical contact with a tray inner wall when the tray is in the first position, said mechanical contact controlling and limiting the travel of the tray from the second position to the first position;

wherein the tray is moveable between the first and second positions while the cover is in a closed position and the mouthpiece is in a locked position; and wherein the second hinge segment, and the third hinge segment, when assembled, form mechanically effective hinge.

2. The dry powder inhaler of claim 1, wherein the inhaler is constructed from four parts only, the inhaler body, the mouthpiece, the tray and the cover and where the mouthpiece and the inhaler body function as the locking means for the hinge joining the inhaler body, the mouthpiece and the cover, each of the inhaler body, mouthpiece, tray and cover being of unitary construction.

3. The dry powder inhaler of claim 1, wherein the hinge only constitutes a fully operational and permanent hinge after the first, second, and third hinge segments are assembled together and the mouthpiece is locked into place into the inhaler body.

4. The dry powder inhaler of claim 1, further comprising a rail guide, wherein the tray is movable inside and outside the body along the rail guide for capsule loading or emptying, while the hinged cover is closed.

5. The dry powder inhaler of claim 1, wherein the inhaler when assembled consists of no more than three integral components: the first component being constituted by the mouthpiece and inhaler body locked together to form a single integral component, the second being constituted by the tray and the third being constituted by the cover.

6. The dry powder inhaler according to claim 1, wherein the complementary locking means provided on the mouthpiece and the inhaler body comprises at least one locking pin provided on one of the mouthpiece and inhaler body and at least one complementary recess provided on the other of the mouthpiece and the inhaler body.

\* \* \* \* \*